United States Patent
Ngo et al.

(10) Patent No.: US 10,759,591 B2
(45) Date of Patent: Sep. 1, 2020

(54) DOSAGE MONITORING BASED ON SIGNAL PRESENCE

(71) Applicant: OES Inc., London (CA)

(72) Inventors: Kiet Ngo, London (CA); Michael Reeve, London (CA)

(73) Assignee: oes, INC., London, Ontario (CA)

(*) Notice: Subject to any disclaimer, the term of this patent is extended or adjusted under 35 U.S.C. 154(b) by 89 days.

(21) Appl. No.: 15/982,346

(22) Filed: May 17, 2018

(65) Prior Publication Data

US 2019/0352082 A1    Nov. 21, 2019

Related U.S. Application Data

(60) Provisional application No. 62/537,108, filed on Jul. 26, 2017.

(51) Int. Cl.
| | |
|---|---|
| *A61J 1/03* | (2006.01) |
| *B65D 83/04* | (2006.01) |
| *A61J 7/04* | (2006.01) |
| *G16H 20/13* | (2018.01) |

(52) U.S. Cl.
CPC .......... *B65D 83/0445* (2013.01); *A61J 1/035* (2013.01); *A61J 7/0436* (2015.05); *A61J 7/0418* (2015.05); *B65D 83/0409* (2013.01); *G16H 20/13* (2018.01)

(58) Field of Classification Search
CPC ...... A61J 1/035; A61J 7/0436; A61J 2200/30; B65D 83/0455; B65D 75/54
See application file for complete search history.

(56) References Cited

U.S. PATENT DOCUMENTS

| | | | |
|---|---|---|---|
| 4,617,557 A | 10/1986 | Gordon | |
| 5,412,372 A | 5/1995 | Parkhurst et al. | |
| 6,244,462 B1 | 6/2001 | Ehrensvard et al. | |
| 6,574,166 B2 | 6/2003 | Niemiec | |
| 7,113,101 B2 | 9/2006 | Petersen et al. | |
| 7,552,824 B2 | 6/2009 | Le et al. | |
| 7,937,829 B2 | 5/2011 | Petersen et al. | |
| 8,091,790 B2 | 1/2012 | Mickle et al. | |
| 8,151,990 B2* | 4/2012 | Udo | A61J 1/035 206/531 |
| 8,960,440 B1 | 2/2015 | Kronberg | |
| 9,235,683 B2 | 1/2016 | Robertson et al. | |
| 2010/0049361 A1 | 2/2010 | Bertrand et al. | |

(Continued)

FOREIGN PATENT DOCUMENTS

| | | |
|---|---|---|
| WO | 2011161299 A1 | 12/2011 |
| WO | 2012049446 A1 | 4/2012 |

(Continued)

OTHER PUBLICATIONS

International Search Report and Written Opinion of International Patent Application No. PCT/CA2018/050900 dated Oct. 24, 2018.

*Primary Examiner* — Timothy R Waggoner
(74) *Attorney, Agent, or Firm* — Carlson, Gaskey & Olds, P.C.

(57) ABSTRACT

An example container includes a plurality of package segments, each having a respective conductive lead that is interrupted when its package segment is opened. The container includes a signaling source configured to provide two signals that are distinguishable from each other. A presence of one or both of the signals on a shared return line indicates whether one of the package segments has been opened.

20 Claims, 5 Drawing Sheets

(56) References Cited

U.S. PATENT DOCUMENTS

| | | | |
|---|---|---|---|
| 2010/0089791 A1* | 4/2010 | Rosenbaum | A61J 1/035 206/531 |
| 2012/0024889 A1 | 2/2012 | Robertson et al. | |
| 2014/0039445 A1* | 2/2014 | Austin | G06F 19/3462 604/404 |
| 2015/0148947 A1* | 5/2015 | McConville | G06F 19/3462 700/244 |
| 2016/0137380 A1 | 5/2016 | Kosaka | |
| 2017/0004284 A1* | 1/2017 | Lesau | A61J 1/035 |

FOREIGN PATENT DOCUMENTS

| | | |
|---|---|---|
| WO | 2012110700 A1 | 8/2012 |
| WO | 2012110701 A1 | 8/2012 |

\* cited by examiner

DOSAGE MONITORING BASED ON SIGNAL PRESENCE

CROSS-REFERENCE TO RELATED APPLICATION

This application claims the benefit of U.S. Provisional Application No. 62/537,108, filed Jul. 26, 2017.

TECHNICAL FIELD

The present disclosure relates to a method and apparatus for detecting dispensing of an item from a package.

BACKGROUND

Blister packs are commonly used for dispensing items, such as medication. In many instances, patients are directed to take medication according to a defined schedule. However, the potential for mistakes or incorrect dosing arises when patients are in charge of monitoring their own medication schedule. For example, a patient may choose to skip one or more dosing times, and take more pills than recommended at other dosing times.

Blister pack monitoring systems have been proposed that detect when an item is dispensed from its blister segment. Some systems have provided discrete current traces for each blister pack compartment, and have determined segment access based on differences in current value measurements. Such systems, however, are costly to manufacture.

SUMMARY

An illustrative example container includes a plurality of package segments, each associated with a respective conductive lead that is interrupted when the package segment is opened. The container includes a signaling source configured to provide two signals that are distinguishable from each other. A presence of one or both of the signals on a shared return line for one of the package segments indicates whether one of the package segments has been opened.

An illustrative example container includes a plurality of package segments, each associated with a conductive lead that is interrupted when the package segment is opened. The container includes a plurality of shared return lines, each of which connects to a respective set of conductive leads corresponding to a respective set of package segments. A signaling source is configured, for each set, to provide a first signal to a first conductive lead of the set over a first signal path and provide a second signal to a second conductive lead of the set over a second signal path. A presence of the first signal on the shared return line indicates that the package segment corresponding to the first conductive lead has not been opened, and a presence of the second signal on the shared return line indicates that the package segment corresponding to the second conductive lead has not been opened.

An illustrative example method of determining whether package segments have been opened includes providing a first signal to a first conductive lead of a set of conductive leads over a first signal path, and providing a second signal to a second conductive lead of the set over a second signal path. The method includes determining whether a package segment corresponding to the first conductive lead of the set has been opened based on a presence of the first signal on a shared return line by the set, and determining whether a package segment corresponding to the second conductive lead of the set has been opened based on a presence of the second signal on the shared return line for the set.

The embodiments described herein may be taken independently or in any combination. Features described in connection with one embodiment are applicable to all embodiments, unless such features are incompatible.

DETAILED DESCRIPTION

Example embodiments of this invention include a container, which may be a blister pack, that includes a plurality of package segments and the ability to indicate when the package segments are accessed. Two signals that are distinguishable from each other, such as an alternating current (AC) signal and a direct current (DC) signal, indicate whether a corresponding package segment has been opened.

Figure 1:
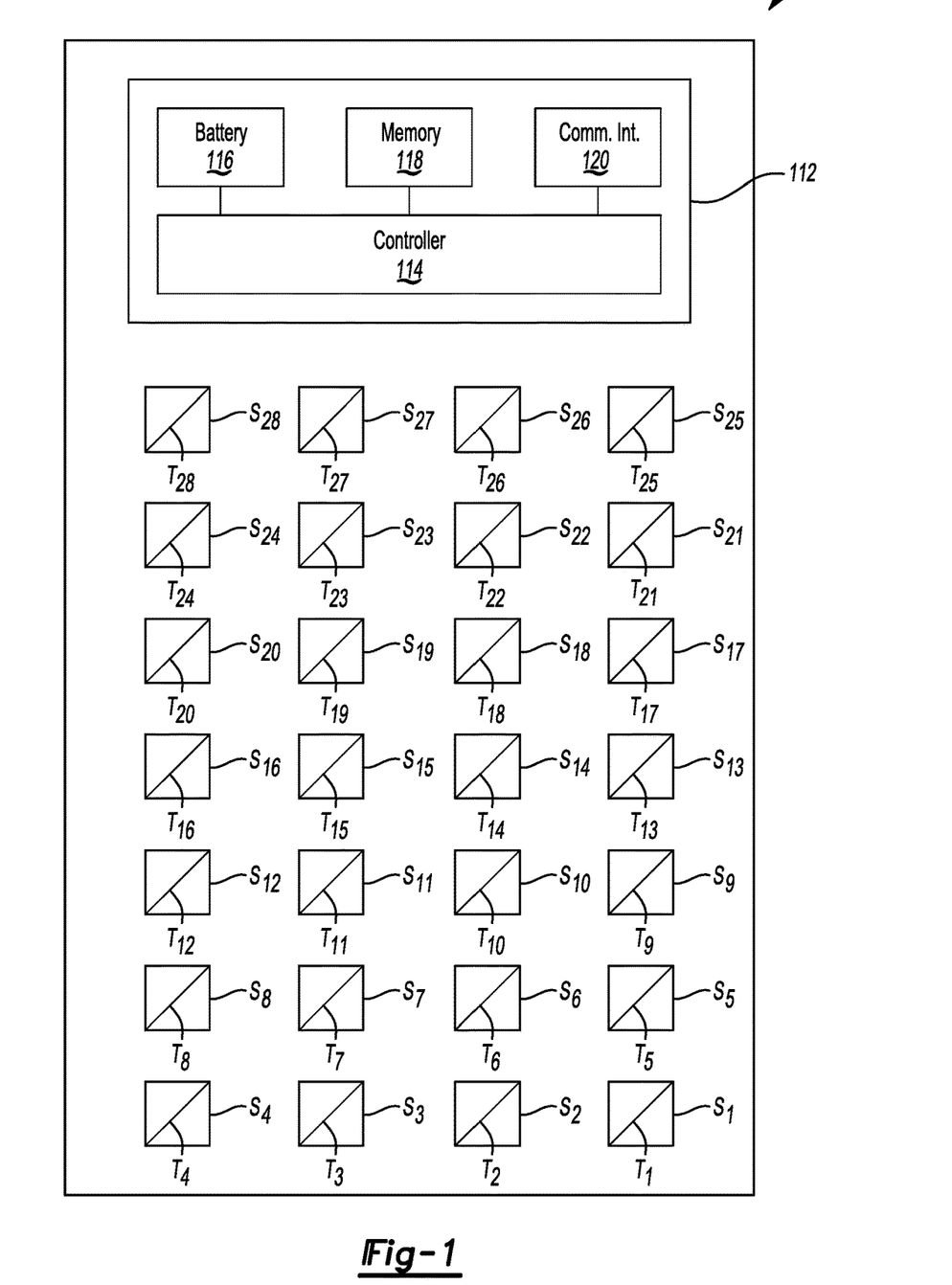
FIG. 1 schematically illustrates an example container having discrete package segments.

FIG. 1 schematically illustrates a container 110, which is a blister pack in some examples. The container 110 includes a plurality of discrete compartments or segments, $S_1$-$S_{28}$. Twenty-eight compartments or segments are included in the illustrated example for discussion purposes. The number of segments may differ on various embodiments.

Each of the segments has a respective associated conductive lead or "trace" $T_1$-$T_{28}$ that is interrupted when its associated package segment is accessed. For example, when a surface or portion of the segment is broken or opened that interrupts the trace.

The container 110 includes a signaling source 112. The signaling source 112 includes a controller 114 that is operatively connected to a battery 116, memory 118, and a communication interface 120. The controller 114 detects when the package segments are accessed based on a flow of current through the respective traces of the package segments. In particular, the signaling source 112 is operable to provide two signals that are distinguishable from each other, such as an AC signal and a DC signal, or two different DC signals (e.g., having different DC voltages). A presence of one or both of the signals on a shared return line for a set of two of the package segments indicates whether a particular one of the corresponding package segments has been opened.

Figure 2:
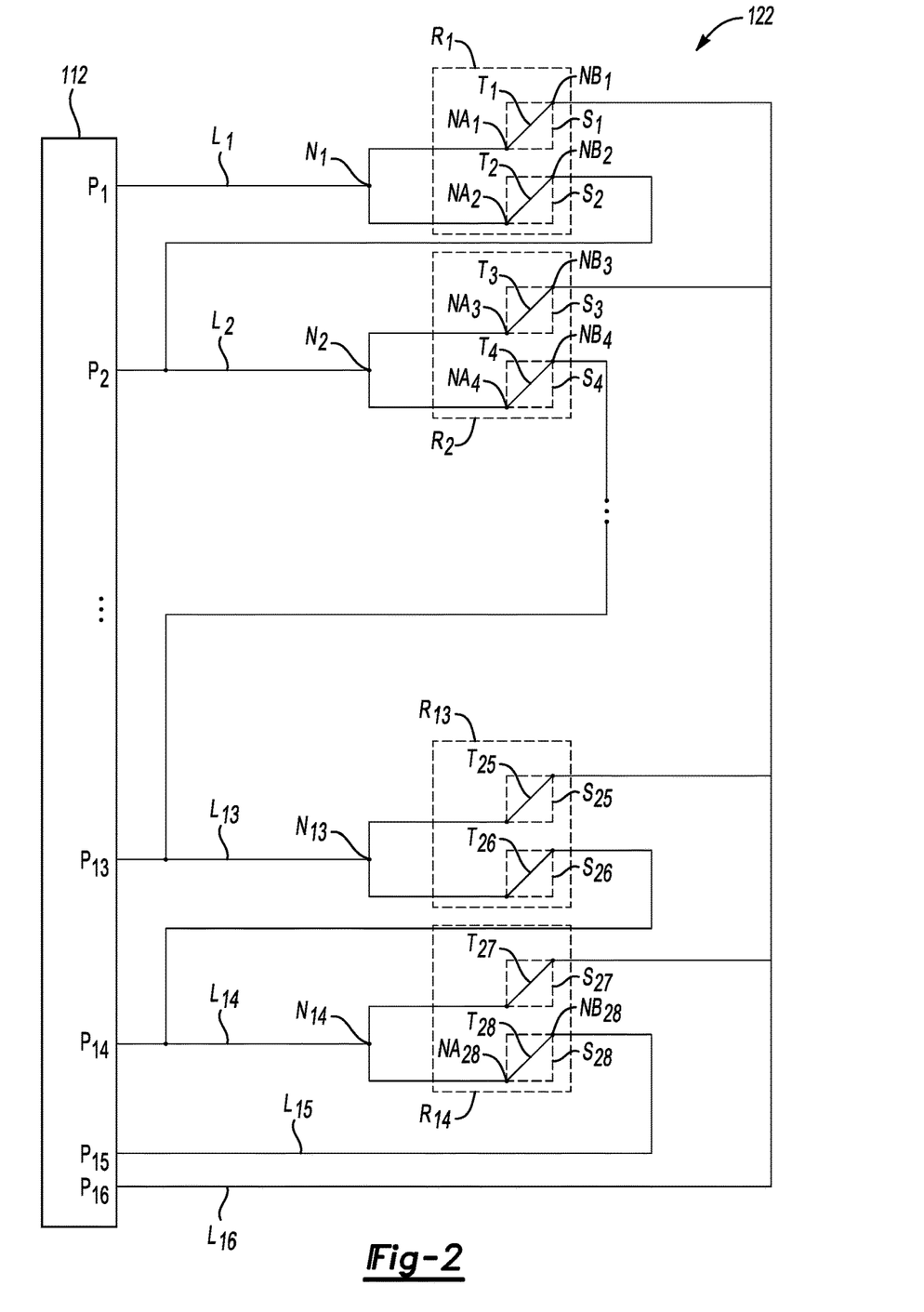
FIG. 2 is an example schematic circuit that can be used for the container of FIG. 1.

FIG. 2 schematically illustrates an example circuit 122 that may be used in connection with the container 110 of FIG. 1. In the example of FIG. 2, the signaling source 112 includes sixteen input/output ports $P_1$-$P_{16}$ that are connected to sixteen lines $L_1$-$L_{16}$. In one example, line $L_{15}$ provides a DC feed, and line $L_{16}$ provides an AC feed. Each of the lines $L_1$-$L_{14}$ is shared by a respective set $R_1$-$R_{14}$ of two package segments and can be used as a return for detecting whether a given package segment has been accessed. In the example of FIG. 2, each set $R_1$-$R_{14}$ includes a pair of package segments. Also, lines $L_2$-$L_{14}$ can be configured as a feed for providing a detection signal. To elaborate on the sharing scheme discussed above, as an example, segments $S_1$ and $S_2$, which use traces $T_1$ and $T_2$, respectively, share line $L_1$ as a return. Package segments $S_3$ and $S_4$, which use traces $T_3$ and $T_4$, respectively, share line $L_2$ as a return, and so on. Thus, instead of having 28 separate return lines for 28 separate package segments $S_1$-$S_{28}$, the 14 shared lines $L_1$-$L_{14}$ can be used as returns instead.

Line $L_1$ connects a first port $P_1$ of the signaling source 112 to a node $N_1$. $N_1$ is the common connection point between segments $S_1$ and $S_2$. Each trace T has two nodes (one at each end), $N_A$ and $N_B$. In reference to Line $L_1$, $T_1$ (corresponding to segment $S_1$) and $T_2$ (corresponding to segment $S_2$) are connected to node $N_1$ at nodes $NA_1$ and $NA_2$, respectively. Trace $T_1$ has a first node $NA_1$ connected to the node $N_1$ and a second node $NB_1$ connected to the feed line $L_{16}$. Trace $T_2$ has a first node $NA_2$ connected to the node $N_1$, and a second node $NB_2$ that is connected to line $L_2$, which is the shared return line of a neighboring set of two package segments $S_3$, $S_4$.

The other sets of package segments are similarly configured, such that the feed line $L_{16}$ is connected to each node NB having an odd numbered subscript (e.g., $NB_1$, $NB_3$, $NB_5$) corresponding to odd numbered segments (e.g., $S_1$, $S_3$, $S_5$, etc.). Each node NB having an even numbered subscript (e.g., $NB_2$, $NB_4$, $NB_6$, etc.) corresponding to even numbered segments (e.g., $S_2$, $S_4$, $S_6$, etc.) is connected to the shared line L of an adjacent set of package segments.

To detect whether the odd numbered traces $T_1$, $T_3$, $T_5$, etc. have been interrupted by access to a corresponding package segment, a first type of test is performed, and to determine whether the even numbered traces $T_2$, $T_4$, $T_6$, etc. have been interrupted by access to a corresponding package segment, a second type of test is performed. In one example, the first type of test is an AC test. Using segment $S_1$ as an example, to detect whether segment $S_1$ has been accessed, the signaling source 112 configures shared line $L_1$ as a return, and pulses feed line $L_{16}$ at a fixed AC frequency. If the AC pulse is detected on the shared line $L_1$, then the trace $T_1$ is intact and its corresponding packaging segment $S_1$ has not been accessed. If AC is not detected on shared line $L_1$, this means that the trace $T_1$ has been interrupted and the corresponding packaging segment $S_1$ has been accessed.

In one example of the first type of test for trace $T_1$, shared lines $L_2$ (and optionally also lines $L_3$-$L_{15}$) are configured as feeds with a DC output that is high, and the signaling source 112 determines that AC is not present on the shared line $L_1$ if only the high DC signal from shared line $L_2$ is detected on line $L_1$. As used herein, a "high" potential means higher than a potential on feed line $L_{16}$ (e.g., higher than a RMS voltage of the signal on line $L_{16}$ and/or higher than an AC peak voltage on line $L_{16}$).

In another example of the first type of test for trace $T_1$, shared line $L_2$ (and optionally also lines $L_3$-$L_{15}$) are configured as feeds with a DC output that is low (e.g., zero potential), and the signaling source 112 determines that AC is not present on the shared line $L_1$ if no current is detected on line $L_1$.

In both of the examples discussed above for the first type of test, if trace $T_1$ is intact, the AC from feed line $L_{16}$ will flow through trace $T_1$ and to line $L_1$, but not to line $L_2$ if $L_2$ is high. When $L_2$ carries a signal that has a higher potential than that of the AC signal, it prevents the AC signal from flowing on line $L_2$ because current from the AC signal will not flow from a low to a high potential. If $L_2$ is at a zero potential, current from the AC signal will not flow through a zero potential.

The remaining other odd numbered package segments $S_3$, $S_5$, $S_7$, etc. (corresponding to traces $T_3$, $T_5$, $T_7$, etc.) can be tested in a similar fashion. Using segment $S_{27}$ as an example, to detect whether that segment has been accessed, the signaling source 112 in one example performs an AC blister test by configuring port $P_{14}$ as a return, and pulsing feed line $L_{16}$ at a fixed AC frequency. If no AC is detected on line $L_{14}$, this means that the trace $T_{27}$ has been interrupted. However, if the AC pulse is detected on the line $L_{14}$ then the trace $T_{27}$ is intact and its corresponding packaging segment $S_{27}$ has not been accessed.

To detect whether the even numbered package segments $S_2$, $S_4$, $S_6$, etc. (corresponding to traces $T_2$, $T_4$, $T_6$, etc.) have been accessed, the signaling source 112 performs the second type of test, which is a DC blister test in some examples. Using segment $S_2$ as an example, the feed line $L_{16}$ is fixed at zero volts (no pulsing). Line $L_2$ is set to high, and port $P_1$ is configured as an input. If no DC is detected on line $L_1$, which is acting or serving as a return in this instance, then trace $T_2$ is broken, and segment $S_2$ has been accessed. However, if DC is detected on line $L_1$, then trace $T_2$ is intact, and segment $S_2$ has not been accessed. The other even numbered package segments can be tested in a similar fashion.

In some examples of the second type of test for package segment $S_2$, each of lines $L_2$-$L_{15}$ carry DC feeds with a high output. In another example of the second type of test for package segment $S_2$, only the shared line that connects to the even numbered package segment is set to high (e.g., only set $L_2$ to high if reading on $L_1$).

To perform the AC test described above, the odd numbered traces $T_1$, $T_3$, $T_5$, etc. can be tested simultaneously or sequentially.

To perform the DC test described above, the even numbered traces $T_2$, $T_4$, $T_6$, etc. can be consecutively tested, or some of them can be tested at the same time (e.g., read on $L_1$, $L_3$, $L_5$, etc. while setting $L_2$, $L_4$, $L_6$, etc. to high).

By using the techniques described above and alternating between performing the first and second types of tests, the signaling source 112 can determine whether each of the package segments $S_1$-$S_{28}$ has been accessed. In this regard, $L_1$ can be used as an AC return line for testing trace $T_1$ and as a DC return line for testing trace $T_2$. Similarly line $L_2$ can be used as an AC return line for testing trace $T_3$ and as a DC return line for testing trace $T_4$, and so forth.

In one example, to provide an AC signal on the feed line $L_{16}$, the signaling source 112 performs pulse width modulation of a DC signal to approximate an AC waveform.

In an alternate configuration for the first type of test, the feed line $L_{16}$ is configured as a DC feed line instead of an AC feed line. In this configuration, the other shared lines that are not configured as returns are set to low, and the odd numbered traces $T_3$, $T_5$, $T_7$, etc. are tested sequentially and not simultaneously. Using trace $T_1$ as an example, in this configuration $P_1$ is set to be an input with line $L_1$ configured as a return, line $L_{16}$ is configured as a DC feed with a constant high output. If DC is not detected on shared line $L_1$ under these conditions, trace $T_1$ has been interrupted and the corresponding packaging segment $S_1$ has been accessed. Otherwise, if DC is detected on shared line $L_1$, then trace $T_1$ is intact, and the corresponding packaging segment $S_1$ has not been opened or accessed.

In one such example, the second type of signal is still a DC signal, but has a different voltage (e.g., 5 volts DC) than the DC signal on feed line $L_{16}$ (e.g., 10 volts DC), and the signals are not provided simultaneously. Of course, other DC voltages could be used. In one example where the first and second signals are both DC signals, a first DC signal is provided on line $L_{16}$ (e.g., 10 volt DC signal), the signal source 112 performs a measurement on pin $P_1$ and determines that trace $T_1$ is intact if the 10 volts DC signal is detected, and is not intact if 0 volts DC is measured. The second DC signal is provided on line $L_2$ from pin $P_2$ (e.g., a 5 volt DC signal), the signaling source 112 performs a measurement on pin $P_1$ and determines that trace $T_2$ is intact if the 5 volts DC signal is detected, and is not intact if 0 volts DC is measured. In one example, the odd numbered traces can be tested simultaneously through the signal on line $L_{16}$, and the even numbered traces are tested at a different time than the odd numbered traces.

As discussed above, in the signals provided in the first and second types of tests are distinguishable from each other. In one example discussed above, the first type of test is an AC signal and the signal provided in the second type of signal is a DC signal. In another example discussed above, the signals provided in the first and second types of tests are both DC signals (e.g., having different voltages). In another example, the signals provided in the first and second types of tests are both AC signals (e.g., having different frequencies).

Figure 3:
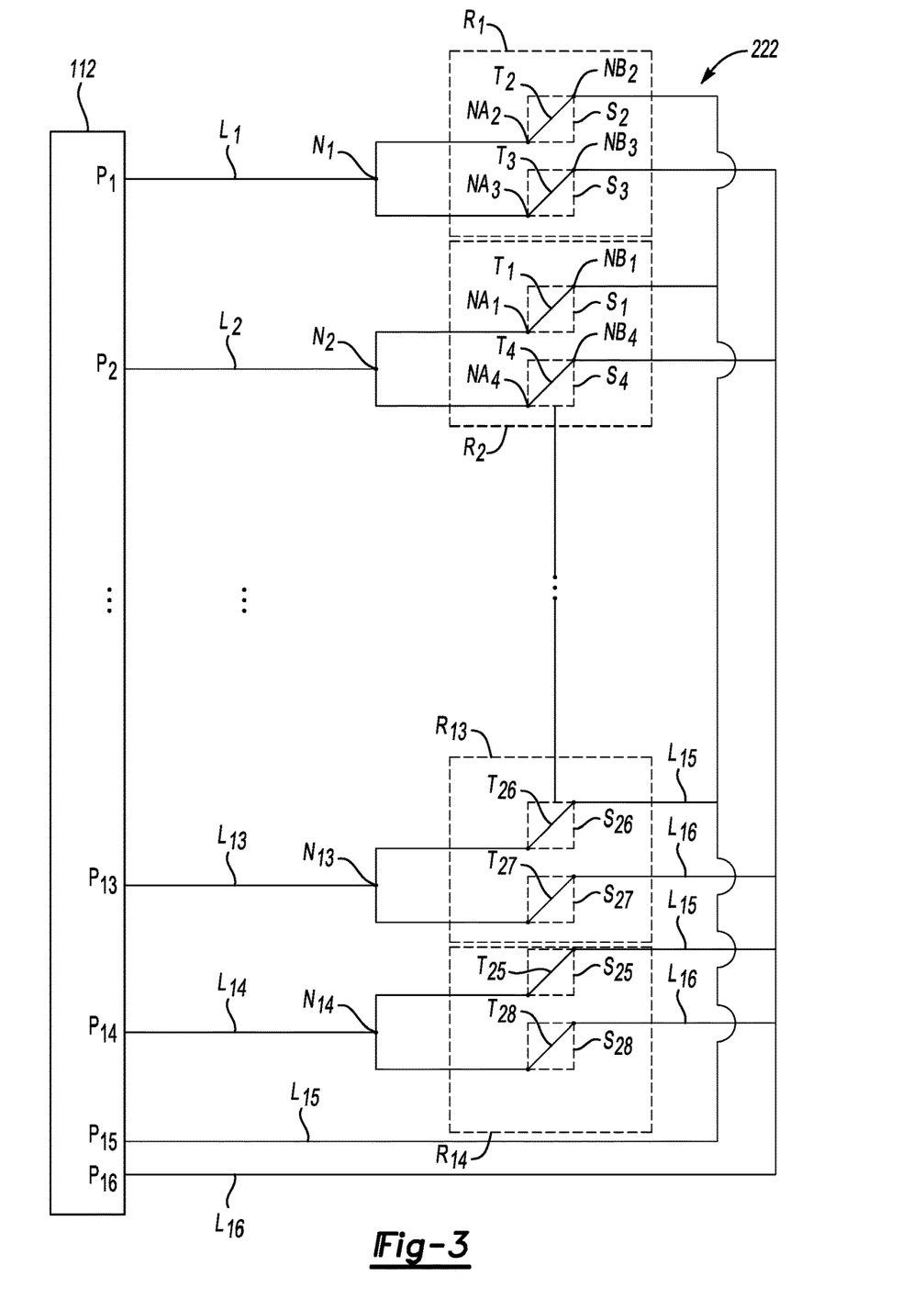
FIG. 3 is another schematic circuit that can be used for the container of FIG. 1.

FIG. 3 schematically illustrates an example circuit 222 that may be used in connection with the container 110 of FIG. 1. In this description, like reference numerals designate like elements where appropriate and reference numerals with the addition of one-hundred or multiples thereof designate modified elements that are understood to incorporate the same features and benefits of the corresponding elements.

In the circuit 222, line $L_1$ still connects pin $P_1$ to node $N_1$, line $L_2$ still connects pin $P_2$ to node $N_2$, and so on. Also, each node $N_1$, $N_2$, etc. connects to the respective NA node of two traces. However, the sets R are arranged differently than in the circuit 122 such that node $N_1$ connects to nodes $NA_2$, $NA_3$, node $N_2$ connects to nodes $NA_1$, $NA_4$, etc. Also, unlike the circuit 122, the NB nodes in the circuit 222 are not connected to the shared line of an adjacent pair of package segments. Instead, line $L_{15}$ connects to node $NB_2$ of trace $T_2$ and node $NB_1$ of trace $T_1$, and line $L_{16}$ connects to node $NB_3$ of trace $T_3$ and node $NB_4$ of trace $T_4$, and so on. This configuration can be generalized as all nodes NB having subscripts {1, 2, 5, 6, 9, 10, 13, 14, 17, 18, 21, 22, 25, 26} being connected to line $L_{15}$ and all nodes NB having subscripts {3, 4, 7, 8, 11, 12, 15, 16, 19, 20, 23, 24, 27, 28} being connected to line $L_{16}$.

For the first type of test for the circuit 222, line $L_{15}$ is used to test the traces to which it connects (i.e., those having subscripts 1, 2, 5, 6, etc.). For the second type of test, line $L_{16}$ is used to test the traces to which it connects (i.e., those having subscripts 3, 4, 7, 8, etc.). The first test can be an AC or DC test, and likewise, the second test can be either an AC or a DC test. In one example, the first and second tests are performed simultaneously, the signal provided on one of line $L_{15}$ and line $L_{16}$ is an AC signal, and the signal provided on the other of line $L_{15}$ and line $L_{16}$ is a DC signal. In one example, the first and second tests are performed according to a staggered schedule, and the same signal type and voltage level are used on both of lines $L_{15}$ and $L_{16}$.

Although sets R of package segments S have been described above as including two segments per set, it is understood that three or more segments could be used in a given set and could share a single return line. By providing a distinguishable signal to each trace in a given set R, the shared return line could be read to determine which (if any) of the package segments in the set R have been accessed. The tests could use AC signals, DC signals, or a combination thereof, as described above.

In some examples, the traces T are created using a conductive ink. As will be discussed in greater detail below, the precise resistance of each trace is unimportant because the signaling source 112 can accurately detect package access without relying on any specific resistance value.

If one were to measure the precise current or voltage differences resulting from various traces being opened, and one wanted to use conductive inks, more expensive conductive inks would have to be used, such as silver inks, because they can achieve more consistent resistance values within a narrow tolerance. Without using such expensive inks, it is very difficult to achieve consistent resistance values amongst traces, and if such values differ by a small amount, a method based on specific current or voltage measurement could result in inaccurate determinations of whether segments have been accessed.

Embodiments of this invention, by relying on the presence of at least one of the first and second type of signal, which are distinguishable from each other, can include less expensive conductive inks, such as carbonate inks, if desired because the specific resistance value is of little importance. Consider an example in which a controller determined how many package segments had been accessed based on how much current measurements change over time. If such a system used conductive traces, then a tight tolerance would be needed to accurately determine how many segments had been accessed. That is not the case with the circuits described above, because signal presence or absence is all that is needed for detection. Accordingly, less expensive conductive inks can be used with the circuits discussed above. Of course conductive traces could be used other than conductive inks if desired.

Figure 4:
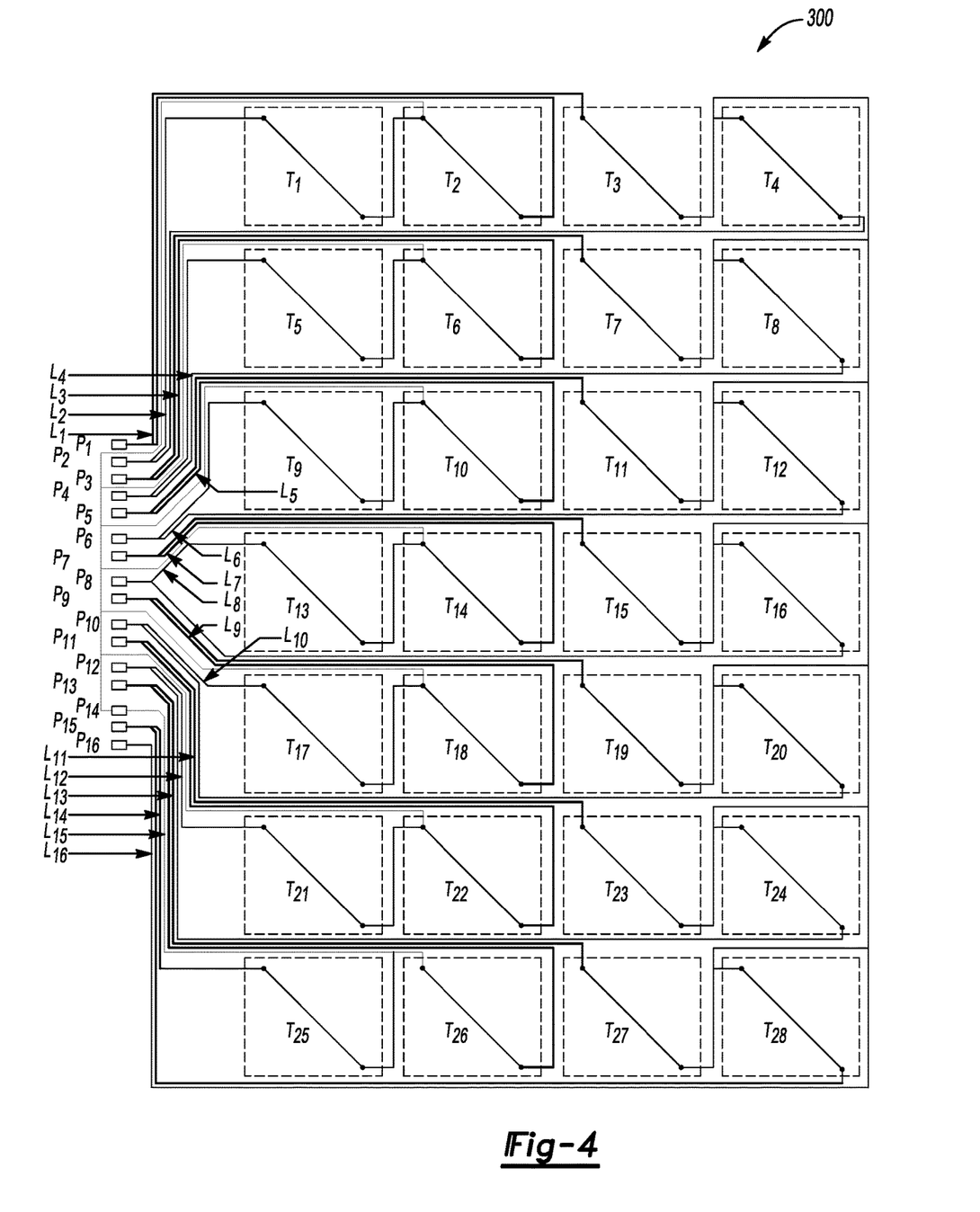
FIG. 4 illustrates an example physical layout for conductive lines of the circuit schematic of FIG. 3.

FIG. 4 illustrates an example physical layout 300 of the lines $L_1$-$L_{16}$ for the circuit 222 for a blister pack. As shown in FIG. 4, twenty eight blister pack traces $T_1$-$T_{28}$ are multiplexed onto shared lines for detecting blister pack segment access.

Figure 5:
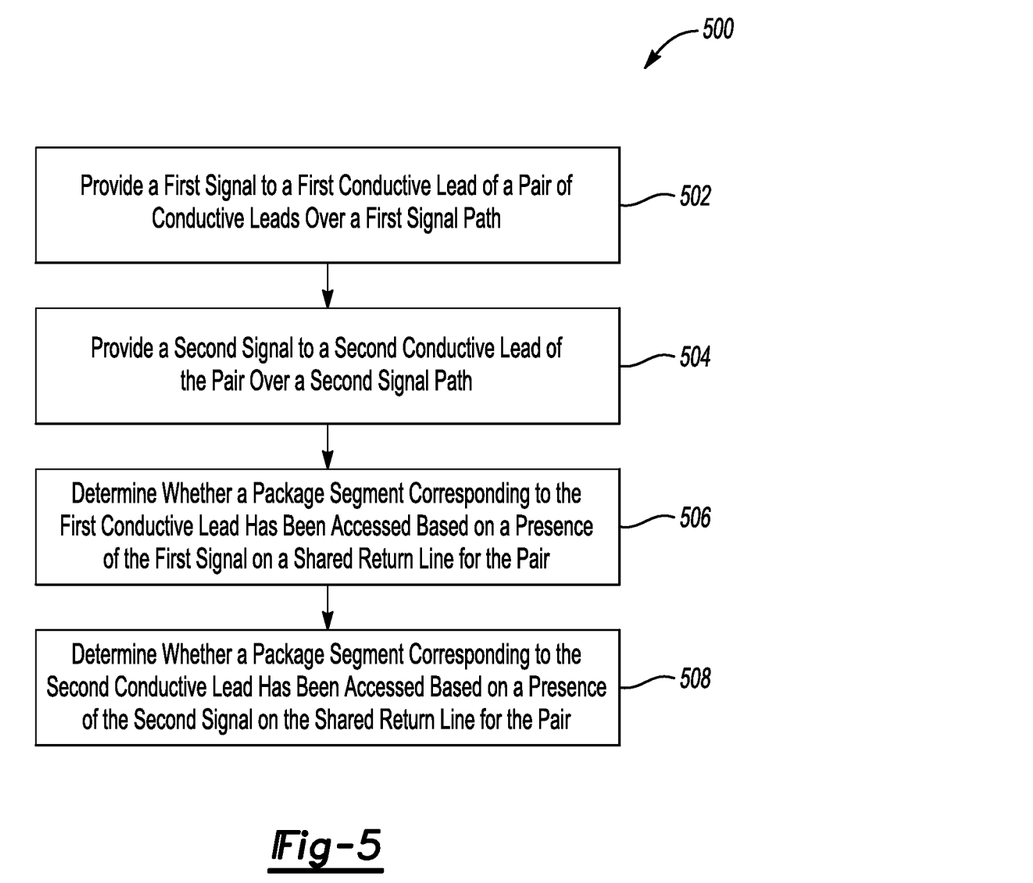
FIG. 5 schematically illustrates an example method of determining whether package segments have been accessed.

FIG. 5 summarizes an example method of determining whether package segments S have been accessed in a flowchart diagram 500. A first signal is provided to a first conductive lead of a pair of conductive leads over a first signal path at 502. A second signal is provided to a second conductive lead of the pair over a second signal path at 504. A determination is made whether a package segment S corresponding to the first conductive lead has been accessed based on a presence of the first signal on a shared return line for the pair at 506. If the first signal is present the segment is unopened. If, on the other hand, the first signal is not present that segment was opened or accessed. A similar determination is made whether a package segment corresponding to the second conductive lead of the pair has been accessed based on a presence of the second signal on the shared return line for the set at 508.

Referring again to FIG. 1, the controller 114 includes processing circuitry, and may include one or more microprocessors, microcontrollers, application specific integrated circuits (ASICs), or the like, for example. The battery 116 powers the controller 114, memory 118, and communication interface 120.

The memory 118 can include at least one of volatile memory elements (e.g., random access memory (RAM, such as DRAM, SRAM, SDRAM, VRAM, etc.)) and non-volatile memory elements (e.g., ROM, flash memory, etc.). In one example, the memory 118 stores program instructions that configure the controller 114 to implement the signaling and detection techniques discussed above. In the same or another example, the memory 118 stores records of when various package segments $S_1$-$S_{28}$ were opened. In one such example, the controller 114 is configured to compare those records to a dosing schedule to detect whether a user has complied with or violated the dosing schedule. In some embodiments the controller 114 generates an output, such as a warning, when inappropriate or unscheduled access occurs.

The communication interface 120 is configured to facilitate communication with an external computing device. In some examples, the communication interface 120 includes a transceiver operable to use one or more wireless signaling protocols (e.g., Bluetooth, Wi-Fi, or a cellular communication protocol such as LTE, GSM, or any other 3GPP-based protocol). In some examples, the communication interface includes a connector for communicating through a wired connection (e.g., a USB connector). In some examples, the signaling source 112 transmits a real-time feed of when segments are accessed in addition to or as an alternative to maintaining a long term saved record in memory 118 of when those accesses occur.

Although blister packs have been discussed as one type of container for which the techniques explained above are useful, it is understood that those techniques could also be applied to other types of packaging.

Also, although example embodiments have been disclosed, a worker of ordinary skill in this art would recognize that the description is illustrative rather than limiting. Certain modifications would come within the scope of the disclosed embodiments. For that reason, the following claims should be studied to determine the scope and content of legal protection.

What is claimed is:

1. A container comprising:
a plurality of package segments, each associated with a respective conductive lead that is interrupted when the package segment is opened; and
a signaling source configured to provide two signals that are distinguishable from each other, wherein a presence of one or both of the signals on a shared return line indicates whether one of the package segments has been opened, wherein the signaling source is configured to provide the two signals as DC signals having different voltages, as AC signals having different frequencies, or is configured to provide a first one of the signals as an AC signal and a second one of the signals as a DC signal;
wherein the conductive leads are arranged in sets, each set including a respective first conductive lead and a respective second conductive lead, and for each set, a respective first node of the first and second conductive lead both connect to a common node, and a respective second node of the first and second conductive lead each have a separate signal path to the signaling source.

2. The container of claim 1, wherein the container includes a plurality of shared return lines, each shared return line being associated with a respective one of the sets and providing a connection between the common node of the associated set and the signaling source for determining the two signals.

3. The container of claim 2, wherein the signaling source is configured to:
determine that a first conductive lead of one of the sets has not been opened based on presence of a first of the two signals on the shared return line associated with the first conductive lead; and
determine that a second conductive lead of the one of the sets has not been opened based on presence of a second of the two signals on the shared return line associated with the second conductive lead.

4. The container of claim 3, wherein two signals are both DC signals or are both AC signals.

5. The container of claim 2, wherein:
the separate signal path of the first conductive lead of each set provides a first one of the two signals that are distinguishable from each other.

6. The container of claim 5, wherein the separate signal path of the second conductive lead of each set includes the shared return line of a different set and provides a second one of the two signals that are distinguishable from each other.

7. The container of claim 5, wherein the separate signal path of the second conductive lead provides a second one of the two signals that are distinguishable from each other.

8. The container of claim 2, wherein the container includes X of the package segments, X of the conductive leads, and Y of the shared return lines, where Y<X.

9. The container of claim 1, wherein the respective conductive leads include a conductive ink.

10. The container of claim 1, wherein the plurality of package segments are blister pack segments.

11. A container comprising:
a plurality of package segments, each associated with a respective conductive lead that is interrupted when the package segment is opened; and
a signaling source configured to provide two signals that are distinguishable from each other, wherein a presence of one or both of the signals on a shared return line indicates whether one of the package segments has been opened;
wherein a first one of the two signals is an AC signal, and a second one of the two signals is a DC signal.

12. A container comprising:
a plurality of package segments, each associated with a conductive lead that is interrupted when the package segment is opened;
a plurality of shared return lines, each of which connects to a respective set of conductive leads corresponding to a respective set of package segments; and
a signaling source that, for each set, provides a first signal to a first conductive lead of the set over a first signal path and provides a second signal to a second conductive lead of the set over a second signal path that is separate from the first signal path, wherein the signals differ from each other at the signaling source, and wherein the signaling source is configured to provide the two signals as DC signals having different voltages, as AC signals having different frequencies, or is configured to provide a first one of the signals as an AC signal and a second one of the signals as a DC signal;
wherein a presence of the first signal on the shared return line indicates that the package segment corresponding to the first conductive lead has not been opened, and a presence of the second signal on the shared return line indicates that the package segment corresponding to the second conductive lead has not been opened.

13. The container of claim 12, wherein, for each set:
the first signal path includes a first shared signaling line that is coupled to the signaling source and is coupled to the first conductive lead of each set and provides the first signal; and
the second signal path includes a second shared signaling line that is coupled to the signaling source and the second conductive lead of each set and provides the second signal.

14. The container of claim 13, wherein:
for each set, the first signal path includes a first shared signaling line that is coupled to the signaling source and is coupled to the first conductive lead of each set; and
for some of the sets, the second signal path includes a shared return line of a different set.

15. The container of claim 12, wherein the first signal is an AC signal, and the second signal is a DC signal.

16. The container of claim 12, wherein the first and second signals are both DC signals or are both AC signals.

17. The container of claim 12, wherein the conductive leads include a conductive ink.

18. A method of determining whether package segments have been opened, comprising:
providing a first signal to a first conductive lead of a set of conductive leads over a first signal path;
providing a second signal to a second conductive lead of the set over a second signal path that is separate from the first signal path;
determining whether a package segment corresponding to the first conductive lead has been opened based on a presence of the first signal on a shared return line for the set; and
determining whether a package segment corresponding to the second conductive lead has been opened based on a presence of the second signal on the shared return line;
wherein the first signal and the second are DC signals having different voltages, the first signal and the second signal are AC signals having different frequencies, or the first signal is an an AC signal and the second signal is DC signal.

19. The method of claim 18, wherein the first signal is an AC signal, and the second signal is a DC signal.

20. The method of claim 18, wherein the first and second signals are both DC signals or are both AC signals.

* * * * *